United States Patent [19]

Duffett

[11] Plant 5,166

[45] Dec. 27, 1983

[54] CHRYSANTHEMUM PLANT

[75] Inventor: William E. Duffett, Salinas, Calif.

[73] Assignee: Yoder Brothers, Inc., Barberton, Ohio

[21] Appl. No.: 340,108

[22] Filed: Jan. 18, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Mellow and particularly characterized as to uniqueness by the combined characteristics of flat capitulum form; daisy capitulum type; dark yellow ray floret color; diameter across face of capitulum ranging from 70 to 90 mm. at maturity; uniform nine week photoperiodic flowering response to short days; tall plant height when grown single stem; 15 to 20 cm. peduncles on open, normally terminal sprays, and slow development of tight green discs.

3 Drawing Figures

The present invention comprises a new and distinct cultivar of *Chrysanthemum morifolium,* Ramat., hereinafter referred to by the cultivar name Mellow.

Mellow is a product of a planned breeding program which had the objective of creating new chrysanthemum cultivars for cut spray mum programs with daisy capitulum type, dark yellow ray floret color, nine week flowering response, and having the ability to produce commercially acceptable quality in year round programs. Such traits in combination were not present in previously available commercial cultivars.

Mellow was originated from a cross made in a controlled breeding program in Salinas, Calif. in 1978. The female parent was the cultivar identified as #72097002 (Tantalizer, U.S. Plant Pat. No. 3,906), a bronze daisy originated from a hybridization of two unnamed seedlings. The male parent of Mellow was the cultivar identified as #76182017, a yellow daisy originated from a cross between #70009008 (Sophisticate, U.S. Plant Pat. No. 3944) and #70038041 (Gem, U.S. Plant Pat. No. 3907).

Mellow was discovered and selected as one flowering plant within the progeny of the stated cross by William E. Duffett on Feb. 23, 1979 in a controlled environment in Salinas, Calif.

The first act of asexual reproduction of Mellow was accomplished when vegetative cuttings were taken from the initial selection in August, 1979 in a controlled environment in Salinas, Calif. by a technician working under formulations established and supervised by William E. Duffett.

Horticultural examination of selected units initiated January, 1980 has demonstrated that the combination of characteristics as herein disclosed for Mellow are firmly fixed and are retained through successive generations of asexual reproduction.

Mellow has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Mellow which in combination distinguish this chrysanthemum as a new and distinct cultivar:

(1) flat capitulum form;

(2) daisy capitulum type;

(3) dark yellow ray floret color;

(4) diameter across face of capitulum ranging from 70 to 90 mm. at maturity.

(5) uniform nine week photoperiodic flowering response to short days;

(6) tall plant height;

(7) open, terminal spray with long (15 to 20 cm.) peduncles; and (8) slow development of tight green discs.

The accompanying photographic drawings depict typical foliage and inflorescence characteristics of Mellow. Sheet 1 is a color photograph of a stem of Mellow grown as a cut spray, with colors being as accurate as possible with renditions of this type. Sheet 2 is a black and white photograph of three views of the inflorescence of Mellow. Sheet 3 shows the top and underside of the foliage of Mellow in three stages of growth.

Of the many commercial cultivars known to the present inventors, the most similar in comparison to Mellow is Florida Marble, U.S. Plant Pat. No. 3288. Reference is made to attached Chart A which compares certain characteristics of Mellow to those same characteristics of Florida Marble.

In comparison to Florida Marble, Mellow has deeper yellow ray floret color, with superior color retention and a slower rate of oxidation; its spray formation is generally more terminal with fewer low crowns formed within the spray; it has a larger diameter across the face of the capitulum by 10 to 20 mm., and taller plant height by approximately 10 cm., and has an improved tolerance of high temperature which results in a response approximately one week faster than Florida Marble during summer periods.

In the following description, color references are made to The Royal Horticultural Society Colour Chart. The color values were determined between 10:00 and 11:00 A.M. on Oct. 20, 1981 under 150 foot-candle light intensity of Salinas, Calif.

Classification:

*Botanical.—Chrysanthemum morifolium,* Ramat., cv Mellow.

*Commercial.*—Cut Daisy Spray.

1. Inflorescence:

A. *Capitulum.—Form: Flat. Type: Daisy. Diameter across face:* 70 to 90 mm.

B. *Corolla of ray floret.*—Color (General Tonality From A Distance of Three Meters): Yellow; approximately 8-A. color (abaxial): 6-A and 6-B (immature) to 8-A and 8-B (mature). Color (adaxial): 5-C and 5-D (immature) to 4-B and 4-C (mature).

C. *Corolla of Disc florets.*—Color (mature): 9-B. Color (immature): 151-C.

D. *Reproductive organs.*—Androecium: Present disc florets only; scant pollen. Gynoecium: Present both ray and disc florets.

II. Plant:

A. *General appearance.*—Height: Tall, 70 to 80 cm., as a flowering plant from a rooted cutting, with no long days for March through November flowerings and maintaining a minimum nightly 14 hour continuous dark period.

B. *Foliage.*—Color (abaxial): 137-A to 137-B. Color (adaxial): 138-A to 138-B. Shape: Deeply lobed and coarsely serrated.

CHART A

COMPARISON OF MELLOW AND FLORIDA MARBLE

| CULTIVAR | RAY FLORET COLOR | CAPITULUM FORM AND TYPE | SPRAY FORMATION |
|---|---|---|---|

CHART A-continued

COMPARISON OF MELLOW AND FLORIDA MARBLE

| | | | |
|---|---|---|---|
| MELLOW | Deep Yellow with minimum oxidation | Flat Daisy | Terminal 15 to 20 cm peduncles |
| FLORIDA MARBLE | Light Yellow with rapid oxidation | Flat Daisy | Frequently compound 15 to 20 cm peduncles |

| CULTIVAR | DIAMETER ACROSS FACE OF CAPITULUM | PLANT HEIGHT | FLOWERING RESPONSE PERIOD |
|---|---|---|---|
| MELLOW | 70 to 90 mm. | Tall 70 to 80 cm. | 9 Week |
| FLORIDA MARBLE | 60 to 70 mm. | Medium 60 to 70 cm. | 9 Week |

COMPARISONS MADE OF PLANTS GROWN AS SINGLE STEM CUT SPRAYS WITH NO LONG DAYS IN SALINAS, CALIFORNIA

I claim:

1. A new and distinct plant of *Chrysanthemum morifolium,* Ramat., known by the cultivar name of Mellow, as described and illustrated, and particularly characterized as to uniqueness by the combined characteristics of flat capitulum form; daisy capitulum type; dark yellow ray floret color; diameter across face of capitulum ranging from 70 to 90 mm. at maturity; uniform nine week flowering response; tall plant height when grown single stem; 15–20 cm. peduncles on open, normally terminal sprays, and slow development of tight green discs.

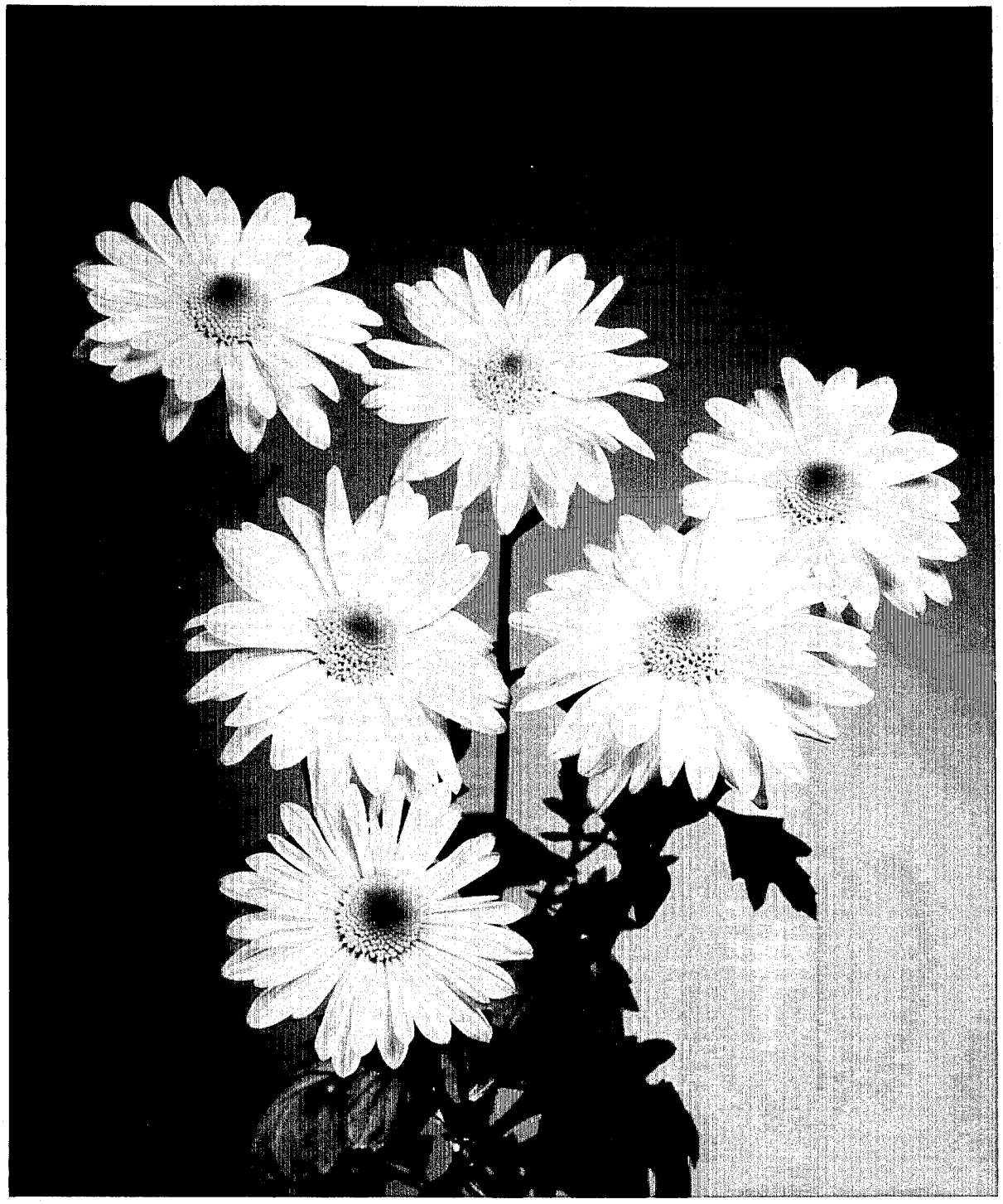

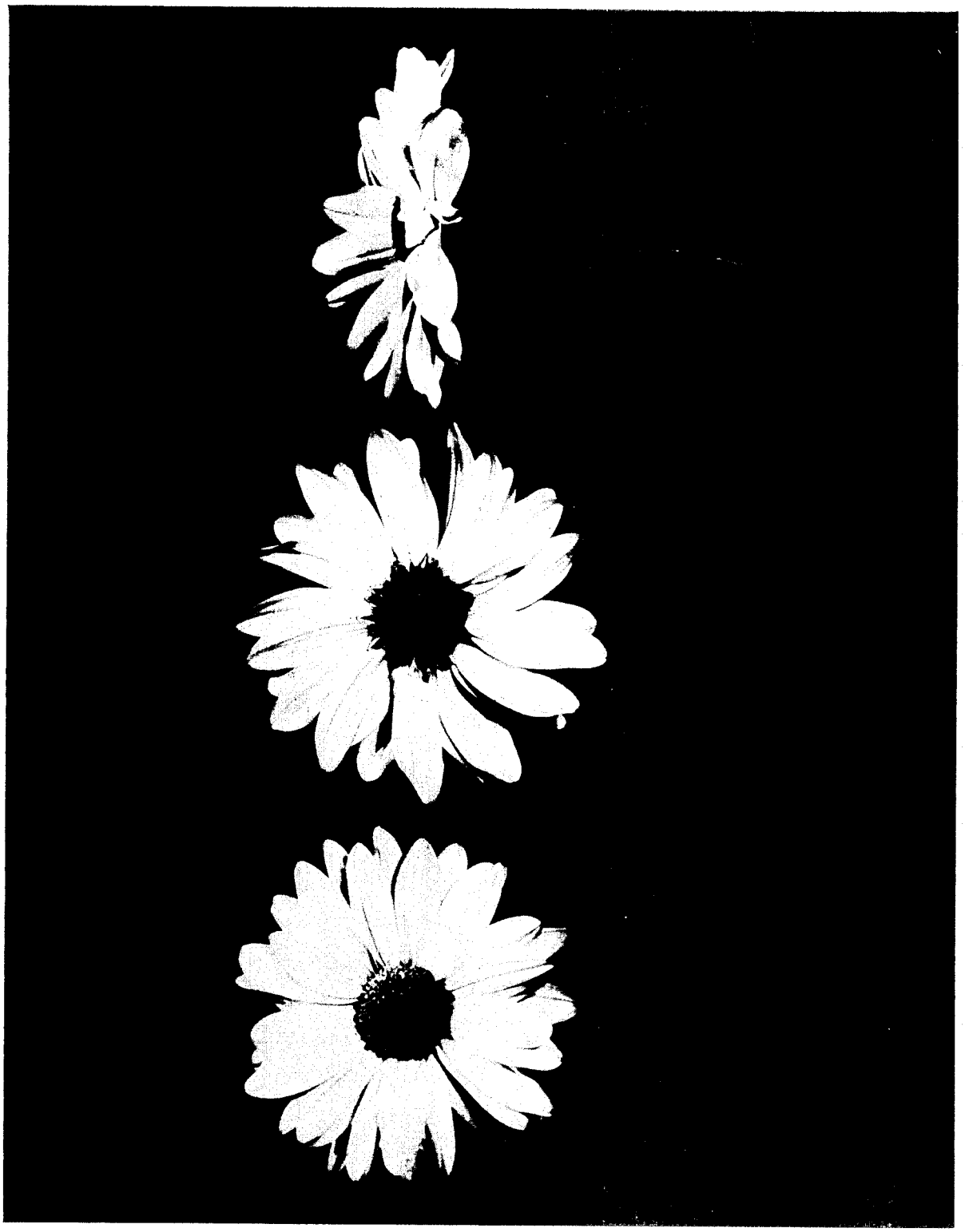

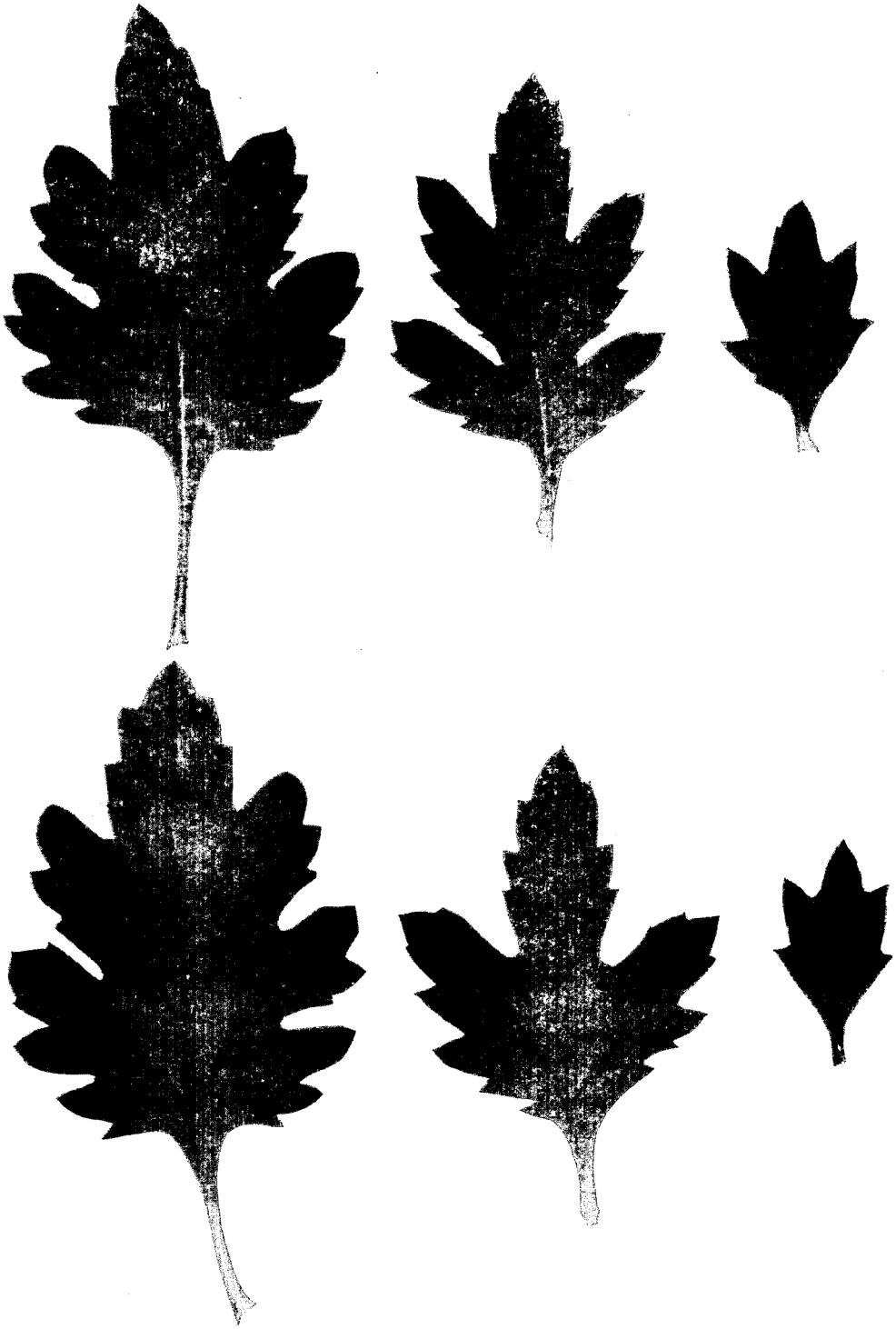

* * * * *